US006555644B2

(12) United States Patent
Ko et al.

(10) Patent No.: US 6,555,644 B2
(45) Date of Patent: Apr. 29, 2003

(54) MULTI-REACTIVE SILICON COMPOUND HAVING POLYALKYLENEGLYCOL SUBSTITUENTS AND SYNTHETIC METHOD THEREOF

(75) Inventors: YoungHoon Ko, Taejeon (KR); EunKyoung Kim, Taejeon (TW)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 09/880,601

(22) Filed: Jun. 13, 2001

(65) Prior Publication Data

US 2002/0103322 A1 Aug. 1, 2002

(30) Foreign Application Priority Data

Nov. 28, 2000 (KR) ......................................... 2000-71158

(51) Int. Cl.[7] .............................................. C08G 77/08
(52) U.S. Cl. ............................. 528/15; 528/29; 528/31; 556/435
(58) Field of Search ........................... 556/435; 528/15, 528/31, 29

(56) References Cited

U.S. PATENT DOCUMENTS

| 5,194,553 | A | | 3/1993 | Freeburne et al. ............ 528/12 |
|---|---|---|---|---|
| 5,340,899 | A | | 8/1994 | Altes ............................ 528/34 |
| 5,373,079 | A | | 12/1994 | Altes ............................ 528/34 |
| 5,391,794 | A | * | 2/1995 | Jung et al. .................... 556/435 |
| 5,527,934 | A | * | 6/1996 | Jung et al. .................... 556/431 |
| 5,858,468 | A | | 1/1999 | Byrd ............................ 427/387 |
| 5,981,070 | A | | 11/1999 | Ishizaki et al. ................ 428/47 |
| 6,005,036 | A | | 12/1999 | Carrozza et al. ............. 524/265 |
| 6,060,559 | A | | 5/2000 | Feng et al. ................... 525/100 |
| 6,271,406 | B1 | * | 8/2001 | Abele et al. ................. 556/431 |

\* cited by examiner

Primary Examiner—Margaret G. Moore
(74) Attorney, Agent, or Firm—Davidson, Davidson & Kappel, LLC

(57) ABSTRACT

A multi-reactive silicon compound has at least one polyalkyleneglycol substituent with the number average molecular weight being 200 to 10,000 as synthesized by reacting an organohalosilane compound having H—Si bonds with a polyalkyleneglycol ether compound having unsaturated substituents in the presence of a hydrosilylation catalyst. The multi-reactive silicon compound having polyalkyleneglycol substituents is very soluble in organic solvents and reactive to living polymeric ions with high thermal stability due to multiple functional groups, and active living groups. Thus, the addition of the multi-reactive silicon compound to a living polymer solution during an anionic or cationic polymerization reaction activates an intense substitution reaction under mild conditions to introduce a third functional group to the end or side chain of the polymer comprising a repeating monomer unit and provide organic-inorganic hybrid polymers.

2 Claims, No Drawings

MULTI-REACTIVE SILICON COMPOUND HAVING POLYALKYLENEGLYCOL SUBSTITUENTS AND SYNTHETIC METHOD THEREOF

TECHNICAL FIELD

The present invention relates to a multi-reactive polyalkyleneglycol ether having polyalkyleneglycol substituents and a synthetic method thereof, and more particularly, to a coupling agent having not only multiple halogen substituents to provide high reactivity with living polymeric anions but also polyalkyleneglycol substituents to enhance compatibility with inorganic fillers, and a synthetic method thereof.

BACKGROUND OF THE INVENTION

Elastomers are easily synthesized and have interesting mechanical properties, including elasticity, and broadly used in various applications such as tires, automobile parts, shock absorbents, shoes and packing. Such elastomers have been developed for organic-inorganic hybrid materials, which are synthesized by mixing silica or glass fibers in vulcanization in order to improve thermal stabilities and mechanical strength.

However, organic polymers are generally incompatible with inorganic fillers in the preparation of such organic-inorganic hybrid materials. To solve this problem, coupling agents have been introduced, or the organic polymers are chemically modified to improve the compatibility with inorganic materials. For the second solution, as well known in the related art, the living polymer is reacted with anion reactive terminators to produce a polymer having inorganophile substituents.

Miura et al., for example, reported a method for preparing a polymer modified with 4-formylphenylalkoxyamine in the anionic polymerization of butadiene (Macromolecules, 1999, 32(25), 8356).

Bronstert et al. disclosed a method for preparing a polymer modified with hydroxyethylamino or hydroxyethylpolyoxyethyleneamino compound (Germany Ger. Offen., 5 pp.).

However, the compounds used in the above documents have still problems of insufficient compatibility with inorganic particles such as silica. In an attempt to solve this problem, many studies have been reported on an organic-inorganic hybrid polymer using silicon compounds. For example, Korean Patent No. 95-704405 discloses a method for bonding hexamethylchlorosiloxane to the end of a living polymer. While the problem related to the phase separation between inorganic fillers and organic polymer is somewhat solved in this method, it is difficult to increase the molecular weight of the polymer and enhance the mechanical properties of the polymer. In order to increase the molecular weight of the polymer and thus improve the mechanical properties of end modified polymers, multi-functional silicon containing terminators are demanded.

On the other hand, silicon containing compounds having halogen as terminal or branched substituents are used as additives in coating, coupling agent, adhesive and silant in order to enhance mechanical properties of the coating surface or the substrate as well as to improve thermal stability and compatibility.

For example, U.S. Pat. No. 5,858,468 discloses a composition comprising a mixture of (a) a polysiloxane having unsaturated groups and (b) a polysiloxane containing reactive Si—H groups. This composition is useful for preparing a coating composition curable at ambient temperature.

U.S. Pat. No. 5,373,079 discloses a polydimethylsiloxane having alkoxy, acyloxy, N-methylbenzamido or alkyl groups. Also, U.S. Pat. No. 5,340,899 discloses a sealant composition comprising a mixture of (a) a polysiloxane having hydroxy end groups and (b) a polysiloxane having vinyl or methylacetamido end groups. This composition is useful for reducing the modulus of the siloxane sealant.

U.S. Pat. No. 5,194,553 discloses a method for preparing an organofunctional-terminated polydiorganosiloxane polymer and a copolymer thereof, which method is useful for making a polydimethyl siloxane having 5-hexenyl end groups. This patent also discloses a method for preparing an organofunctional-terminated polydiorganosiloxane polymer using an organofunctional chlorosilane end-blocker, and a method for preparing an organofunctional-terminated polydiorganosiloxane copolymer using an organofunctional chlorosilane end-blocker and an organofunctional chlorosilane.

These reactive silicon compounds are capable of reacting with at least two living polymers to produce multi-substituted elastomer when they have the functional groups with at least two substituents. However, the polydimethylsiloxane is ready to be decomposed prior to reaction with the living polymer due to its low storage stability and very poor in reactivity with living polymeric anions, which makes it difficult to activate multi-substitution reactions.

Thus there is a need of providing a silicon compound having high storage stability and excellent reactivity.

U.S. Pat. No. 6,005,036 discloses a method for preparing a polysilane compound used as a process stabilizer. Also, the halogen-substituted silicon compounds are widely used in various applications such as adhesion additives (U.S. Pat. No. 6,060,559); water-absorbent agents (U.S. Pat. No. 5,981,070); and coatings. Thus there is a need of providing such a silicon compound containing functional groups such as halogen as well as polar functional groups.

SUMMARY OF THE INVENTION

In an attempt to solve the problems, the inventors of this invention have studied on a synthesis of silicon containing terminators, particularly, silicon compound having polar substituents with excellent compatibility with inorganic fillers, and contrived halosilyl polyalkyleneglycol ether macromers having at least one polyalkyleneglycol substituent.

It is, therefore, an object of the present invention to provide halosilyl polyalkyleneglycol ether macromers having polar functional groups and at least two halogen substituents that can participate in various substitution reactions, more specifically, halosilyl polyalkyleneglycol ether macromers reactive to at least one equivalent of polymers in an anionic or cationic polymerization reaction.

To achieve the above object of the present invention, there is provided a reactive halosilyl polyalkyleneglycol ether containing at least two functional groups with at least one polyalkyleneglycol substituent and at least two halogen substituents, the reactive halosilyl polyalkyleneglycol ether having a number average molecular weight of 200 to 10,000 and being represented by the formula 1, $(X)_a(R)_b(R^1)_c Si$—$C(R^4)(R^5)$—$Si(X)_d(R)_e(R^2)_f$, in which X is a halogen atom selected from the group consisting of F, Cl, Br and I; $R^1$ and $R^2$ are the same or different and independently represent hydrogen, an alkyl group containing 1 to 10 carbon atoms or a $C_1$ to $C_{10}$ alkyl group having F or Cl substituents; $R^4$ and $R^5$ are the same or different and independently represent hydrogen, $Si(X)_a(R)_b(R^1)_c$ or $Si(X)_d(R)_e(R^2)_f$; R is a polyalkyleneglycol group represented by the formula $\{C(R^6)(R^7)CH(R^8)C(R^6)(R^7)Z\}-\{C(R^6)(R^7)C(R^6)(R^7)O\}_g R^9$; $R^6$, $R^7$ and $R^8$ are the same or different and independently represent hydrogen, an alkyl group containing 1 to 10 carbon atoms, or a $C_1$ to $C_{10}$ alkyl group having F or Cl substituents; $R^9$ is methyl or ethyl; Z is oxygen or p-substituted benzene ring ($C_6H_4$); a and d are the same or different and independently represent a number from 1 to 3; b and e are the same or different and independently represent a number from 0 to 2; c and f are the same or different and independently represent a number 0 or 1, wherein a+b+c+d+e+f=6; and g is a number from 1 to 20.

The reactive halosilyl polyalkyleneglycol ether represented by the formula 1 is synthesized by reacting a halogen-substituted silane compound having a Si—H bond as represented by the formula 2, $(X)_a(H)_b(R^1)_c Si-C(R^4)(R^5)-Si(X)_d(H)_e(R^2)_f$ with a polyalkyleneglycol ether having a double bond as represented by the formula 3, $\{C(R^6)(R^7)=C(R^8)C(R^6)(R^7)Z\}-\{C(R^6)(R^7)C(R^6)(R^7)O\}_g R^9$, in which X, Z, $R^1$ to $R^9$ and a to g are as defined above formula 1, in the presence of a hydrosilylation catalyst.

DETAILED DESCRIPTION OF THE PREFERRED EMBODIMENT

Hereinafter, preferred embodiments of the present invention will be described in detail as follows.

The reactive halosilyl polyalkyleneglycol ether represented by the formula 1 is prepared by reacting a silane compound having at least one halogen substituent as represented by the formula 2 with a polyalkyleneglycol derivative having unsaturated groups as represented by the formula 3 in the presence of a hydrosilylation catalyst.

Specific examples of the compound represented by the formula 2 include $Cl_2HSiCH_2SiHCl_2$, $Cl_3SiCH_2SiHCl_2$, 1,1,3,3-tetrachloro-2-(dichlorosilyl)-1,3-disilabutane, $Cl_2MeSiCH_2SiHCl_2$ and $Cl_2HSiCH_2SiClMe_2$, the syntheses of which compounds are disclosed in the reference documents (J. Organomet. Chem., 516, 91 (1996); U.S. Pat. Nos. 5,233,069 and 5,399,740; and Organometallics, 12, 2360 (1993)).

Specific examples of the compound represented by the formula 3 incluae $CH_2=CHCH_2O(CH_2CH_2O)_g CH_3$, $CH_2=CHCH_2O(CH(CH_3)CH_2O)_g CH_3$, $CH_2=CHCH_2O(CH_2CH_2O)_g CH_2CH_3$, $CH_2CHCH_2O(CH(CH_3)CH_2O)_g CH_2CH_3$ and $CH_2=CH-Bz-CH_2CH_2O(CH_2CH_2O)_g CH_3$.

These compounds are synthesized by an industrial method disclosed in the reference document, for example, Makromol, Chem., 182, 1379 (1981), or commercially available from manufacturing companies such as Aldrich.

The compound of the formula 2 has at least one functional group participating in the reaction, and is preferably used at the equivalent ratio with respect to the compound of the formula 3 being 1:1 to 5:1.

Examples of the silylation catalyst include chloroplatinic acid, transition metals, e.g., palladium, rhodium or platinum, and complex compounds, which are all commercially available from manufacturing companies such as Aldrich or synthesized by known methods. Examples of the reaction solvent as used herein may include, if not specifically limited to, organic solvents such as benzene, toluene or xylene.

The silylation temperature is in the range from −20° C. to 150° C., preferably, from room temperature to 120° C. The silylation is conducted in the nitrogen atmosphere with stirring. The silylation time is not specifically limited and may be preferably in the range from about 30 minutes to one week.

After the completion of the reaction and removal of the solvent under vacuum, the resulting material is purified to produce the halosilyl polyalkyleneglycol ether represented by the formula 1.

The halosilyl polyalkyleneglycol ether of the formula 1 according to the present invention has halogen groups highly reactive to the compounds containing living anionic or cationic groups, hydroxyl groups or amine groups, and thus can participate in various reactions.

For example, the halosilyl polyalkyleneglycol ether of the formula 1 is highly reactive to living anionic or cationic polymers to form a covalent bond between the polymers and silicon compounds, and can be used in the preparation of a polymer modified with silicon compounds containing polyalkyleneglycol. Also, the polyalkyleneglycol group enhances compatibility with inorganic fillers, e.g., silica, carbon black, metal oxides, metal powder, glass fiber or other ceramics, as well as mechanical properties, and can be used for organic-inorganic hybrid composite materials.

In particular, the halosilyl polyalkyleneglycol ether of the present invention is very soluble in normal organic solvents such as benzene, toluene, xylene, acetonitrile, sulfolane, propylene carbonate and acetone, and highly reactive to living polymeric ions or radicals generated by anionic, cationic or radical initiators. The polymeric ions or radicals may include reaction products comprising monomers such as aromatic or aliphatic diene with unsaturated groups, or polysiloxane or cyclosiloxane.

For example, the tetrachlorosilicon compound having triethyleneglycol substituents prepared according to the present invention is reacted with polystyrene-butadiene living polymeric ions generated from an anionic polymerization reaction to produce a modified polystyrene-butadiene-silane polymer having at least three polystyrene-butadiene polymeric substituents and two triethyleneglycol substituents.

Therefore, the multi-reactive silicon compound having polyalkyleneglycol groups prepared according to the present invention can be used for preparation of modified polymers, which is usable for compositions of various use purposes, such as conductive rubber, tire, sticking agent, coating solution, sealant, and paint.

Hereinafter, the present invention will be described in detail by way of examples, which are not intended to limit the scope of the present invention.

EXAMPLE 1

8.5 g of $Cl_2HSiCH_2SiHCl_2$ was dissolved in 120 ml of toluene under the nitrogen atmosphere, followed by addition of 0.1 ml of platinum-divinyl-tetramethyldi-siloxane complex (in xylene) and 18 g of $CH_2=CHCH_2O(CH_2CH_2O)_3 CH_3$, and 24 hours of stirring at 80° C. After the completion of the reaction and removal of the solvent from the reactants, the product was dissolved in n-hexane in the argon (Ar) atmosphere and passed through charcoal. The n-hexane and the remaining compound, $Cl_2HSiCH_2SiHCl_2$ were removed to obtain 24 g of $Cl_2\{CH_3O(CH_2CH_2O)_3 CH_2CH_2CH_2\}SiCH_2Si\{CH_2CH_2CH_2(OCH_2CH_2)_3 OCH_3\}Cl_2$.

$^1$H-NMR (CDCl$_3$, ppm): 1.2, 3.3, 3.4~3.6

IR (KBr, cm$^{-1}$): 2958, 2881, 1257(Si—CH$_2$), 1095, 1030, 802(Si—Cl)

EXAMPLES 2 TO 5

Procedures were performed in the same manner as described in Example 1, excepting that the reaction was conducted under the conditions as listed in Table 1 to produce multi-reactive silicon compounds having polyalkyleneglycol substituents (with at least 90% yield). The multi-reactive silicon compounds thus obtained were analyzed by $^1$H-NMR, Si-NMR and FT-IR, the $^1$H-NMR values being presented in Table 1.

ends of a quadrivalent reactive silicon compound having polyalkyleneglycol groups.

To a 10 l autoclave reactor were added 5,000 g of cyclohexane, 100 g of tetrahydrofuran, 200 g of styrene monomer, 800 g of butadiene monomer and 10 mmol of n-butyl lithium. Following the polymerization reaction of one hour, 1.24 g of the polysiloxane compound obtained in Example 2 was added to the reaction mixture, thereby coupling the ends of the polymer. After 10 minutes, 5 ml of a methanol solution (1M cyclohexane solution) was added to

TABLE 1

SYNTHESIS OF MULTI-REACTIVE SILICON COMPOUND HAVING POLYALKYLENEGLYCOL SUBSTITUENTS

| Ex. | Compound (Formula 2) (unit: g) | Compound (Formula 3) (unit: g) | Solvent | Temp (° C.) | Time (hr.) | Yield (g) | $^1$H-NMR (CDCl$_3$, ppm) |
|---|---|---|---|---|---|---|---|
| 1 | Cl$_2$HSiCH$_2$SiHCl$_2$ (8.5) | CH$_2$=CHCH$_2$O(CH$_2$CH$_2$O)$_3$CH$_3$ (18) | Toluene | 80 | 12 | 24 | 1.2, 3.2, 3.4~3.6 |
| 2 | Cl$_2$HSiCH$_2$SiHCl$_2$ (10) | CH$_2$=CHCH$_2$O(CH$_2$CH$_2$O)$_{7.2}$CH$_3$ (19) | Toluene | 80 | 15 | 26 | 1.54, 3.31, 3.43~3.59 |
| 3 | Cl$_3$SiCH$_2$SiHCl$_2$ (12) | CH$_2$=CHCH$_2$O(CH$_2$CH$_2$O)$_3$CH$_3$ (10) | Benzene | 60 | 7 | 18 | 1.55, 3.3, 3.45~3.60 |
| 4 | Cl$_2$HSiCH(SiHCl$_2$)SiHCl$_2$ (13) | CH$_2$=CHCH$_2$O(CH$_2$CH$_2$O)$_3$CH$_3$ (20) | Benzene | 40 | 24 | 29 | 1.34, 3.36, 3.45~3.59 |
| 5 | Cl$_3$SiCH$_2$SiHCl$_2$ (12) | CH$_2$=CHCH$_2$O(CH$_2$CH$_2$O)$_{7.2}$CH$_3$ (19) | Toluene | Reflux | 12 | 28 | 1.55, 3.33, 3.43~3.57 |
| 6 | Cl$_2$HSiCH$_2$SiHCl$_2$ (5) | CH$_2$=CHCH$_2$O(CH$_2$CH$_2$O)$_{7.2}$C(=O)CH$_3$ (20) | Toluene | 80 | 12 | 22 | 1.25, 1.95, 3.53~3.62 |
| 7 | Cl$_2$HSiCH$_2$SiHCl$_2$ (1.1) | CH$_2$=CHCH$_2$O(CH$_2$CH$_2$O)$_{7.5}$SO$_2$CH$_3$ (4.5) | Toluene | Reflux | 8 | 4.9 | 1.30, 3.10, 3.47~3.59 |
| 8 | Cl$_3$SiCH$_2$SiHCl$_2$ (2.5) | CH$_2$=CHCH$_2$O(CH$_2$CH$_2$O)$_{7.5}$SO$_2$CH$_3$ (4.5) | Toluene | Reflux | 12 | 6.0 | 1.52, 3.15, 3.43~3.59 |
| 9 | Cl$_2$HSiCH(SiHCl$_2$)SiHCl$_2$ (1.4) | CH$_2$=CHCH$_2$O(CH$_2$CH$_2$O)$_3$C(=O)CH$_3$ (2.3) | Xylene | 100 | 10 | 3.1 | 1.21, 1.93, 3.31~3.59 |
| 10 | Cl$_2$HSiCH(SiHCl$_2$)SiHCl$_2$ (1.4) | CH$_2$=CHCH$_2$O(CH$_2$CH$_2$O)$_3$C(=O)CH$_3$ (4.6) | Toluene | Reflux | 12 | 3.3 | 1.20, 1.92, 3.30~3.58 |

EXAMPLE 6

Synthesis method of polystyrene-butadiene-polysiloxane having polystyrene-butadiene polymeric substituents to the ends of a quadrivalent reactive silicon compound having polyalkyleneglycol groups.

To a 10 l autoclave reactor were added 5,000 g of cyclohexane, 100 g of tetrahydrofuran, 200 g of styrene monomer, 800 g of butadiene monomer and 10 mmol of n-butyl lithium. Following the polymerization reaction of one hour, 0.71 g of the multi-reactive silicon compound having polyalkyleneglycol groups obtained in Example 1 was added to the reaction mixture, thereby coupling the ends of the polymer. After 10 minutes, 5 ml of a methanol solution (1M cyclohexane solution) was added to the reaction mixture to completely eliminate the active portions of the polymer.

The final product thus obtained was a styrene-butadiene random copolymer of which the coupled styrene content was 20%, the 1,2-vinyl bond content of the butadiene unit 57%, the coupling number (C/N) 4, the coupling efficiency (C/E) 50%, the number average molecular weight about 250,000.

EXAMPLE 7

Synthesis method of polystyrene-butadiene-polysiloxane having polystyrene-butadiene polymeric substituents to the the reaction mixture to completely eliminate the active regions of the polymer.

The final product thus obtained was a styrene-butadiene random copolymer of which the coupled styrene content was 20%, the 1,2-vinyl bond content of the butadiene unit 57%, the coupling number (C/N) 4, the number average molecular weight about 250,000.

EXAMPLE 8

Synthesis method of polystyrene-butadiene-polysiloxane having polystyrene-butadiene polymeric substituents to the ends of a quadrivalent reactive silicon compound having polyalkyleneglycol groups.

To a 10 l autoclave reactor were added 5,000 g of cyclohexane, 100 g of tetrahydrofuran, 200 g of styrene monomer, 800 g of butadiene monomer and 10 mmol of n-butyl lithium. Following the polymerization reaction of one hour, 1.02 g of the polysiloxane compound obtained in Example 5 was added to the reaction mixture, thereby coupling the ends of the polymer. After 10 minutes, 5 ml of a methanol solution (1M cyclohexane solution) was added to the reaction mixture to completely eliminate the active regions of the polymer.

The final product thus obtained was a styrene-butadiene random copolymer of which the coupled styrene content was 20%, the 1,2-vinyl bond content of the butadiene unit 57%, the coupling number (C/N) 5, the number average molecular weight about 300,000.

As described above, the multi-reactive silicon compound having polyalkyleneglycol substituents according to the present invention is highly reactive to anions or living polymeric anions contains living groups having a proper activity, so that it can be added to a living polymer solution to participate in multi-substitution under a mild condition, thereby not only introducing a third functional group to the end or side chain of the polymer comprising a repeating monomer unit but also providing various novel compounds including hydroxyl compounds. In particular, the multi-reactive silicon compound of the present invention is useful in synthesis methods of polyalkyleneglycol-substituted polymers, coating agent, surface-modifier, spot, adhesive or dendrimer, as well as organic-inorganic hybrid polymers.

What is claimed is:

1. A compound containing at least two functional groups with at least one polyalkyleneglycol substituent and at least two halogen substituents, the compound having a number average molecular weight of 200 to 10,000 and being represented by the formula $(X)_a(R)_b(R^1)_c Si-C(R^4)(R_5)-Si(X)_d(R)_e(R^2)_f$, in which:

X is a halogen atom selected from the group consisting of F, Cl, Br and I;

$R^1$ and $R^2$ are the same or different and independently represent hydrogen, an alkyl group containing 1 to 10 carbon atoms, or a $C_1$ to $C_{10}$ alkyl group having F or Cl substituents;

$R^4$ and $R^5$ are the same or different and independently represent hydrogen, $Si(X)_a(R)_b(R^1)_c$ or $Si(X)_d(R)_e(R^2)_f$;

R is a polyalkyleneglycol group represented by the formula $\{C(R^6)(R^7)CH(R^8)C(R^6)(R^7)Z\}-\{C(R^6)(R^7)C(R^6)(R^7)O\}_g R^9$;

$R^6$, $R^7$ and $R^8$ are the same or different and independently represent hydrogen, an alkyl group containing 1 to 10 carbon atoms, or a $C_1$ to $C_{10}$ alkyl group having F or Cl substituents;

$R^9$ is methyl or ethyl;

Z is oxygen or p-substituted benzene ring ($C_6H_4$);

a and d are the same or different and independently represent a number from 1 to 3;

b and e are the same or different and independently represent a number from 0 to 2;

c and f are the same or different and independently represent a number 0 or 1, wherein a+b+c+d+e+f=6; and g is a number from 1 to 20.

2. A method for preparing a compound represented by the formula 1, $(X)_a(R)_b(R^1)_c Si-C(R^4)(R^5)-Si(X)_d(R)_e(R^2)_f$, in which:

X is a halogen atom selected from the group consisting of F, Cl, Br and I;

$R^1$ and $R^2$ are the same or different and independently represent hydrogen, an alkyl group containing 1 to 10 carbon atoms, or a $C_1$ to $C_{10}$ alkyl group having F or Cl substituents;

$R^4$ and $R^5$ are the same or different and independently represent hydrogen, $Si(X)_a(R)_b(R^1)_c$ or $Si(X)_d(R)_e(R^2)_f$;

R is a polyalkyleneglycol group represented by the formula $\{C(R^6)(R^7)CH(R^8)C(R^6)(R^7)Z\}-\{C(R^6)(R^7)C(R^6)(R^7)O\}_g R^9$;

$R^6$, $R^7$ and $R^8$ are the same or different and independently represent hydrogen, an alkyl group containing 1 to 10 carbon atoms, or a $C_1$ to $C_{10}$ alkyl group having F or Cl substituents;

$R^9$ methyl or ethyl;

Z is oxygen or p-substituted benzene ring ($C_6H_4$);

a and d are the same or different and independently represent a number from 1 to 3;

b and e are the same or different and independently represent a number from 0 to 2;

c and f are the same or different and independently represent a number 0 or 1, wherein a+b+c+d+e+f=6; and g is a number from 1 to 20, the method comprising reacting a halogen-substituted silane compound represented by the formula 2, $(X)_a(H)_b(R^1)_c Si-C(R^4)(R^5)-Si(X)_d(H)_e(R^2)_f$ with at least one polyalkyleneglycol derivative having unsaturated substituents and being represented by the formula 3, $\{C(R^6)(R^7)=C(R^8)C(R^6)(R^7)Z\}-\{C(R^6)(R^7)C(R^6)(R^7)O\}_g R^9$, in which X, Z, $R^1$ to $R^9$ and a to g are as defined above formula 1, in the presence of a hydrosilylation catalyst at the temperature of −20 to 150° C. for 30 minutes to 1 week.

\* \* \* \* \*